(12) United States Patent
Yoshida

(10) Patent No.: US 8,933,054 B2
(45) Date of Patent: *Jan. 13, 2015

(54) LOW MOLECULAR WEIGHT HYALURONIC ACID AND/OR SALT THEREOF, METHOD FOR PRODUCING SAME, AND COSMETIC PREPARATION AND FOOD COMPOSITION CONTAINING SAME

(75) Inventor: Takushi Yoshida, Kunitachi (JP)

(73) Assignee: Q.P. Corporation (JP)

( * ) Notice: Subject to any disclaimer, the term of this patent is extended or adjusted under 35 U.S.C. 154(b) by 1848 days.

This patent is subject to a terminal disclaimer.

(21) Appl. No.: 11/909,267

(22) PCT Filed: Mar. 17, 2006

(86) PCT No.: PCT/JP2006/305356
§ 371 (c)(1),
(2), (4) Date: Dec. 23, 2008

(87) PCT Pub. No.: WO2006/101030
PCT Pub. Date: Sep. 28, 2006

(65) Prior Publication Data
US 2009/0215719 A1   Aug. 27, 2009

(30) Foreign Application Priority Data
Mar. 22, 2005   (JP) .................................. 2005-081571

(51) Int. Cl.
| | | |
|---|---|---|
| A01N 43/04 | (2006.01) |
| A61K 31/715 | (2006.01) |
| C08B 37/00 | (2006.01) |
| C07H 5/04 | (2006.01) |
| C07H 5/06 | (2006.01) |
| A61Q 19/00 | (2006.01) |
| A23L 1/056 | (2006.01) |
| A23L 1/30 | (2006.01) |
| A23L 2/52 | (2006.01) |
| A61K 8/73 | (2006.01) |
| C08B 37/08 | (2006.01) |
| A61Q 19/02 | (2006.01) |

(52) U.S. Cl.
CPC .................. *A61Q 19/00* (2013.01); *A23L 1/056* (2013.01); *A23L 1/30* (2013.01); *A23L 2/52* (2013.01); *A61K 8/735* (2013.01); *C08B 37/0072* (2013.01); *A61Q 19/02* (2013.01)
USPC .......................................... 514/54; 536/55.1

(58) Field of Classification Search
CPC ....... A61K 8/735; A61Q 19/00; A61Q 19/02; A23L 1/056; C08B 37/0072
USPC .......................................... 514/54; 536/55.1
See application file for complete search history.

(56) References Cited

U.S. PATENT DOCUMENTS

| 5,605,891 | A | 2/1997 | Prino et al. |
| 6,018,035 | A * | 1/2000 | Hai et al. ...................... 536/22.1 |
| 6,020,484 | A | 2/2000 | Callegaro et al. |
| 7,014,860 | B1 * | 3/2006 | Kawata et al. ................ 424/422 |
| 8,367,818 | B2 * | 2/2013 | Yoshida et al. .............. 536/55.1 |
| 2002/0192205 | A1 | 12/2002 | Michon et al. |
| 2004/0097465 | A1 | 5/2004 | Asari et al. |
| 2005/0090661 | A1 | 4/2005 | Asari et al. |
| 2005/0267068 | A1 * | 12/2005 | Back et al. ...................... 514/54 |
| 2006/0135439 | A1 | 6/2006 | Kato et al. |
| 2007/0224277 | A1 * | 9/2007 | Borbely et al. ............... 424/489 |

FOREIGN PATENT DOCUMENTS

| CN | 1525869 A | 9/2004 |
| CN | 1563108 A | 1/2005 |
| CN | 1563109 A | 1/2005 |
| EP | 0 889 055 | 1/1999 |
| GB | 2 249 315 | 5/1992 |
| JP | 62-292710 | 12/1987 |
| JP | 63-057602 | 3/1988 |
| JP | A-63-57602 | 3/1988 |
| JP | 63-150209 | 6/1988 |
| JP | 63-150209 A | 6/1988 |
| JP | 63-150210 | 6/1988 |
| JP | 63-150210 A | 6/1988 |
| JP | 63-270701 | 11/1988 |
| JP | 63-301826 | 12/1988 |
| JP | 1266102 | 10/1989 |
| JP | A-1-266102 | 10/1989 |
| JP | 04-158796 | 6/1992 |
| JP | 04-505774 | 10/1992 |
| JP | 4-505774 A | 10/1992 |
| JP | 05-111367 | 5/1993 |
| JP | 05-255045 | 10/1993 |
| JP | 5-255045 A | 10/1993 |
| JP | 06-157322 | 6/1994 |
| JP | 06-157604 | 6/1994 |
| JP | 09-208420 | 8/1997 |

(Continued)

OTHER PUBLICATIONS

Machine translation of JP05-255045 (1993) [online] [Retrieved May 7, 2011] Retrieved from the internet <http://dossier1.ipdl.inpit.go.jp/AIPN/odse_top_dn.ipdl?N0000=7400>.*

(Continued)

*Primary Examiner* — Scarlett Goon

(74) *Attorney, Agent, or Firm* — Harness, Dickey & Pierce, P.L.C.

(57) ABSTRACT

A low-molecular-weight hyaluronic acid and/or its salt is obtained by dispersing hyaluronic acid and/or its salt in an acidic water-containing medium.

17 Claims, No Drawings

(56) References Cited

FOREIGN PATENT DOCUMENTS

| | | |
|---|---|---|
| JP | 9-208420 A | 8/1997 |
| JP | 10-195107 | 7/1998 |
| JP | A-11-124401 | 11/1999 |
| JP | 2000-502141 | 2/2000 |
| JP | 2000-502141 A | 2/2000 |
| JP | 2000-095660 | 4/2000 |
| JP | 2000-102362 | 4/2000 |
| JP | 2000-102362 A | 4/2000 |
| JP | 3113056 | 9/2000 |
| JP | 2001-081103 | 3/2001 |
| JP | 2001-81103 A | 3/2001 |
| JP | 2001-270829 | 10/2001 |
| JP | 2001-270829 A | 10/2001 |
| JP | 2002-145750 | 5/2002 |
| JP | 2002-145750 A | 5/2002 |
| JP | 2004-043645 | 2/2004 |
| JP | 2004-43645 A | 2/2004 |
| JP | 2004-337151 | 12/2004 |
| JP | 2004-337151 A | 12/2004 |
| JP | 2005-110675 | 4/2005 |
| JP | 2005-110675 A | 4/2005 |
| JP | 2005-110675 A1 | 4/2005 |
| JP | 2006-036666 | 2/2006 |
| JP | 3767627 | 2/2006 |
| JP | 3767627 B1 | 2/2006 |
| KR | 2000-0072318 | 12/2000 |
| WO | 91-04279 | 4/1991 |
| WO | 97-22629 | 6/1997 |
| WO | WO 01/57093 A1 * 8/2001 ............. C08B 37/08 |
| WO | 02-04471 | 1/2002 |
| WO | 02-074318 | 9/2002 |
| WO | WO 02/074318 A1 | 9/2002 |
| WO | 2004-084912 | 10/2004 |
| WO | 2006-101030 | 9/2006 |

OTHER PUBLICATIONS

Machine translation of JP11-124401 (1999) [online] [Retrieved Jul. 5, 2011] Retrieved from the internet <http://dossier1.ipdl.inpit.go.jp/AIPN/odse_top_dn.ipdl?N0000=7400>.*

"Hyaluronidase" Product Information Sheet from Sigma (2002) [online] [Retrieved Jul. 5, 2011] Retrieved from the internet <http://www.sigmaaldrich.com/etc/medialib/docs/Sigma/Product_Information_Sheet/2/h3884pis.Par.0001.File.tmp/h3884pis.pdf>.*

"Protein Concentration and Sample Clarification" from Millipore [online], [retrieved Jan. 28, 2012]. Retrieved from the internet <http://www.millipore.com/immunodetection/id3/concentration>.*

N. Jouon, et al, "Hydration of Hyaluronic Acid as a Function of the Counterion Type and Relative Humidity", Carbohydrate Polymers, vol. 26, pp. 69-73 (1995).

Claes Melander, et al., "Heterogeneous Hydrolysis of Hyaluronic Acid in Ethanolic HCl Slurry", Carbohydrate Polymers, vol. 82, No. 3, pp. 874-879 (2010).

Yuko Inoue, et al., "Preparation, by Chemical Degradation of Hyaluronic Acid, of a Series of Even- and Odd-Numbered Oligosaccharides having a 2-Acetamido-2-Deoxy-D-Glucose and a D-Glucuronic Acid Residue, Respectively, at the Reducing End", Carbohydrate Research, vol. 141, No. 1, pp. 99-110 (1985).

Nils Hartler, et al., "Heterogeneous Hydrolysis of Cellulose with High Polymer Acids. Part 3. The Acid Hydrolysis of Cellulose with Finely Divided Cation-Exchange Resin in the Hydrogen Form", Journal of Polymer Science, vol. 56, No. 1, pp. 425-434 (1962).

L. Kudlacek et al., "The Effect of Heterogeneous Hydrolysis on the Structure of Cellulose", Polymer Science U.S.S.R., vol. 6, No. 4, pp. 648-655 (1964).

Yu. V. Brestkin, et al., "Heterogeneous Degradation of Cellulose", Polymer Science U.S.S.R., vol. 11, No. 11, pp. 2771-2778 (1969).

Tawada, Akira et al., "Large-Scale Preparation, Purification, and Characterization of Hyaluronan Oligosaccharides From 4-MERS to 52-MERS", Glycobiology, vol. 12, No. 7, pp. 421-426 (2002).

Jeanloz, Roger W. and Dorothy A., The Degradation of Hyaluronic Acid by Methanolysis, vol. 3, No. 1, Jan. 1964, pp. 121-122.

Pall Corporation, "Ultrafiltration Fundamentals," pp. 1-3 (2011).
Supplementary Search Report for EP 06 729 346.4 dated May 4, 2011 (3 pages).
1st Office Action for EP 06 729 346.4 dated Nov. 15, 2011 (2 pages).
Extended European Search Report for Application No. EP 12 00 1414.7 dated May 14, 2012 (5 pages).
English Translation of 1st Office Action for Korean Application No. 10-2007-7024107 issued Oct. 25, 2010 (1 page).
English Translation of 2nd Office Action for Korean Application No. 10-2007-7024107 issued Jan. 17, 2011 (4 pages).
English Translation of Decision to Refuse a Patent for Korean Application No. 10-20077034107 issued Oct. 25, 2011 (1 page).
Decision to Maintain the Decision to Refuse a Patent for Korean Application No. 10-2007-7034107 issued May 19, 2011 (3 pages).
English translation of 1st Office Action for Chinese Application No. 2006-80008997.9 issued Nov. 27, 2009 (3 pages).
English translation of 2nd Office Action for Chinese Application No. 2006-80008997.9 issued Dec. 3, 2010 (2 pages).
English translation of 3rd Office Action for Chinese Application No. 2006-80008997.9 issued Feb. 24, 2011 (2 pages).
English translation of 1st Office Action for Chinese Application No. 2011-10008110.9 issued Feb. 2, 2012 (7 pages).
English translation of 1st Office Action for Japanese Application No. 2005-081571 dated Jun. 3, 2009 (5 pages).
English translation of 2nd Office Action for Japanese Application No. 2005-081571 dated Jan. 20, 2010 (6 pages).
English translation of 3rd Office Action for Japanese Application No. 2005-081571 dated May 18, 2010 (2 pages).
English translation of 1st Office Action for Japanese Application No. 2009-178669 dated May 22, 2012 (3 pages).
English translation of International Preliminary Report on Patentability for Application No. PCT/JP2006/305356 issued Aug. 12, 2008 (8 pages).
Supplementary European Search Report for Application No. 07 71 4683 mailed Jan. 19, 2011 (2 pages).
European Search Opinion for Application No. 07 71 4683 Date Unknown (2 pages).
English translation of 1st Office Action for European Application No. 07 714 683.5 mailed Oct. 27, 2011 (2 pages).
English translation of 1st Office Action for Chinese Application No. 2007-80006415.8 issued Dec. 1, 2010 (8 pages).
English translation of International Preliminary Report on Patentability for Application No. PCT/JP2007/053183 issued Aug. 26, 2008 (8 pages).
English translation of 1st Office Action for Japanese Application No. 2008-502722 dated Jun. 12, 2012 (5 pages).
T. Laurent et al., "Fractionation of Hyaluronic Acid, The Polydispersity of Hyaluronic Acid From the Bovine Vitreous Body", Biochemica et Biophysica Acta, 42, pp. 476-485, (1964).
Shoten, Horokawa, English translation of "The Japanese Pharmacopoeia", 14th Edition, (2006) (12 pages).
C. Yomota et al., "Evaluation of Molecular Weights of Hyaluronate Preparations by Multi-Angle Light Scattering", Bull. National Institute Health Sci., 121, 030-033 (2003) (5 pages).
English version of "The Japanese Pharmacopoeia, Fourteenth Edition", (2001) (6 pages).
"Protein Concentration and Sample Clarification" from Millipore [online], [retrieved Jan. 28, 2012 by U.S. PTO]. Retrieved from the internet <http://www.millipore.com/immunodetection/id3/concentration>.
"Hyaluronidase" Product Information Sheet from Sigma (2002) [online] [Retrieved Jul. 5, 2011 by U.S. PTO]. Retrieved from the internet <http://www.sigmaaldrich.com/etc/medialib/docs/Sigma/Product_Information_Sheet/2/h3884pis.Par.0001.File.tmp/h3884pis.pdf>.
Armstrong et al., "Biotechnology Techniques", vol. 9, No. 7, pp. 491-496, Jul. 1995.
NHV Corporation, EPS Electron Beam Processing System (Brochure and Partial Translation), 4 pages (Sep. 2008).
European Search Report from EP07714683.5, mailed Feb. 8, 2011.
International Search Report, from PCT/JP2007/053183, mailed May 22, 2007.
English computer translation of Japanese Patent Application No. 2005-110675, (2005).

* cited by examiner

LOW MOLECULAR WEIGHT HYALURONIC ACID AND/OR SALT THEREOF, METHOD FOR PRODUCING SAME, AND COSMETIC PREPARATION AND FOOD COMPOSITION CONTAINING SAME

TECHNICAL FIELD

The present invention relates to hyaluronic acid and/or its salt of which the molecular weight has been reduced without impairing the color tone, a method for producing the same, and a cosmetic and a food composition containing the same.

BACKGROUND ART

Hyaluronic acid is a mucopolysaccharide which exists in a living body (particularly subcutaneous tissue). Hyaluronic acid or its salt has been widely used as a raw material for cosmetics due to high moisture retention properties. It has been confirmed that oral administration of hyaluronic acid or its salt compensates for a decrease in hyaluronic acid content of a living body to improve moisture retention, elasticity, and flexibility of the skin. Therefore, hyaluronic acid and its salt are added to various types of food.

However, hyaluronic acid is a polysaccharide having an extremely high molecular weight and a high viscosity. Therefore, when hyaluronic acid is added in an amount exceeding a specific amount, preparation may become difficult due to high viscosity, or the viscosity of the resulting cosmetics or food may be affected, whereby the feel during use may deteriorate or the texture may be impaired.

In order to reduce the viscosity of hyaluronic acid while maintaining its functions, a method has been developed which reduces the molecular weight of the hyaluronic acid (JP-A-63-57602). This application discloses a method of decomposing hyaluronic acid by treatment with an alkali or an acid to reduce the molecular weight of the hyaluronic acid. However, since this method requires that the alkali or acid treatment conditions be made severe in order to reduce the molecular weight, it is difficult to obtain a low-molecular-weight hyaluronic acid. According to this method, hyaluronic acid browns under strongly acidic or strongly basic conditions. Since brown hyaluronic acid is not suitable as a raw material for cosmetics or food, purification for decolorization may be necessary, or it may be difficult to decolorize the hyaluronic acid by purification to such an extent that the hyaluronic acid can be used as the raw material for cosmetics or food.

DISCLOSURE OF THE INVENTION

An object of the invention is to provide a low-molecular-weight hyaluronic acid and/or its salt which is stably produced without causing browning, a method for producing the same, and a cosmetic and a food composition containing the same.

In order to achieve the above object, the inventors of the invention have conducted extensive studies on the method of reducing the molecular weight of hyaluronic acid and/or its salt. As a result, the inventors have found that the molecular weight of hyaluronic acid and/or its salt can be reduced to 10,000 or less, for example, without causing the resulting product to brown by dispersing hyaluronic acid and/or its salt in an acidic water-containing medium, whereby a low-molecular-weight hyaluronic acid can be stably obtained. This finding has led to the completion of the invention.

A low-molecular-weight hyaluronic acid and/or its salt according to the invention is obtained by dispersing hyaluronic acid or its salt in an organic solvent containing an acid and water.

In the low-molecular-weight hyaluronic acid and/or its salt according to the invention, the hyaluronic acid and/or its salt may be dispersed with heating. The expression "dispersed with heating" includes "dispersing the hyaluronic acid or its salt by adding the hyaluronic acid or its salt to the organic solvent containing an acid and water with heating" and "maintaining a state in which the hyaluronic acid or its salt is dispersed in the organic solvent containing an acid and water with heating for a specific period of time".

A low-molecular-weight hyaluronic acid and/or its salt according to the invention is obtained by dispersing hyaluronic acid and/or its salt in an acidic water-containing medium, and heating and drying a residue obtained by removing the water-containing medium.

In the low-molecular-weight hyaluronic acid and/or its salt according to the invention, the water-containing medium may have a pH of 2 or less.

In the low-molecular-weight hyaluronic acid and/or its salt according to the invention, a medium used for the water-containing medium may be at least one medium selected from ethanol, methanol, and acetone.

In the low-molecular-weight hyaluronic acid and/or its salt according to the invention, a 1 wt % aqueous solution of the low-molecular-weight hyaluronic acid and/or its salt may have a kinematic viscosity of 10 $mm^2$/s or less.

In the low-molecular-weight hyaluronic acid and/or its salt according to the invention, a 1 wt % aqueous solution of the low-molecular-weight hyaluronic acid and/or its salt may have a kinematic viscosity of 3 $mm^2$/s or less.

In the low-molecular-weight hyaluronic acid and/or its salt according to the invention, a 1 wt % aqueous solution of the low-molecular-weight hyaluronic acid and/or its salt may have a kinematic viscosity of 2 $mm^2$/s or less.

The low-molecular-weight hyaluronic acid and/or its salt according to the invention may have an L value indicating lightness of 90 or more and a b value indicating hue of 5 or less.

A method for producing a low-molecular-weight hyaluronic acid and/or its salt according to the invention comprises dispersing hyaluronic acid and/or its salt in an acidic water-containing medium.

A cosmetic according to the invention comprises the low-molecular-weight hyaluronic acid and/or its salt according to the invention.

A food composition according to the invention comprises the low-molecular-weight hyaluronic acid and/or its salt according to the invention.

The low-molecular-weight hyaluronic acid and/or its salt according to the invention can be stably produced without causing browning even if the molecular weight is reduced to 10,000 or less, for example. Therefore, the low-molecular-weight hyaluronic acid and/or its salt according to the invention is useful as a raw material for cosmetics, food, and medicine.

For example, when using the low-molecular-weight hyaluronic acid and/or its salt according to the invention as a raw material for cosmetics, the color tone is not impaired even if a large amount of low-molecular-weight hyaluronic acid and/or its salt is added, whereby cosmetics exhibiting an excellent feel during use can be obtained. For example, when using the low-molecular-weight hyaluronic acid and/or its salt according to the invention as a raw material for food, the food can be prepared without impairing the color tone, flavor, and texture of the food.

BEST MODE FOR CARRYING OUT THE INVENTION

The invention is described below. In the invention, "%" refers to "mass %".

1. Low-Molecular-Weight Hyaluronic Acid and/or its Salt

A low-molecular-weight hyaluronic acid and/or its salt according to the invention is obtained by dispersing hyaluronic acid and/or its salt in an acidic water-containing medium.

The term "hyaluronic acid" used in the invention refers to a polysaccharide including a repeating unit made up of glucuronic acid and N-acetylglucosamine. The hyaluronic acid salt is not particularly limited. The hyaluronic acid salt is preferably a pharmaceutically acceptable salt. Examples of the hyaluronic acid salt include a sodium salt, a potassium salt, a calcium salt, a zinc salt, a magnesium salt, an ammonium salt, and the like.

1.1. Raw Material

Hyaluronic acid and its salt (hereinafter also called "raw material hyaluronic acid and its salt") as the raw material for the low-molecular-weight hyaluronic acid and/or its salt according to the invention are generally obtained by extraction (and further purification, if necessary) from a biological tissue such as a cockscomb, an umbilical cord, an eyeball, skin, or cartilage, or a culture obtained by culturing a hyaluronic acid-producing microorganism such as a *Streptococcus* microorganism.

As the raw material hyaluronic acid and its salt used in the invention, the above crude extract or purified product may be used. It is preferable to use a purified product with a purity of hyaluronic acid and/or its salt of 90% or more. When using a raw material hyaluronic acid and its salt with a purity of 90% or more as the raw material for cosmetics or food, the raw material hyaluronic acid and its salt rarely cause a change in color tone or flavor during storage. Therefore, stable cosmetics or food is obtained.

1.2. Low-Molecular-Weight Hyaluronic Acid and/or its Salt

The term "low-molecular-weight hyaluronic acid and/or its salt" according to the invention refers to a product having a molecular weight lower than that of the raw material hyaluronic acid and its salt. For example, the molecular weight of hyaluronic acid and/or its salt extracted from a cockscomb is usually 2,000,000 to 8,000,000. When using hyaluronic acid and/or its salt extracted from a cockscomb as the raw material, the low-molecular-weight hyaluronic acid and/or its salt according to the invention has a molecular weight lower than that of the raw material.

For example, when using the low-molecular-weight hyaluronic acid and/or its salt according to the invention for cosmetics, a food composition, a medicine, or the like, it is preferable that the low-molecular-weight hyaluronic acid and/or its salt according to the invention exhibit a high degree of lightness (brightness) and a low degree of yellowness so that the color of the resulting product is not affected.

The low-molecular-weight hyaluronic acid and/or its salt according to the invention may have an L value indicating the lightness (hereinafter may be simply called "L value") of 90 or more and a b value indicating the hue (hereinafter may be simply called "b value") of 5 or less. The L value and the b value are preferably 92 or more and 4 or less, and more preferably 93 or more and 3.5 or less, respectively.

The L value is a value specifying the lightness of a substance and is indicated by a value between 0 and 100. An L value of 100 indicates the brightest state (completely white), and an L value of 0 indicates the darkest state (completely black).

The b value is a value specifying the hue of a substance. The larger the b value, the higher the degree of yellowness. The smaller the b value, the higher the degree of blueness.

The L value and the b value may be indicated by Lab chromaticity coordinates according to a color difference indication method defined in JIS Z8730. The L value and the b value may be measured using a commercially-available color difference meter. In the invention, the L value and the b value of solid low-molecular-weight hyaluronic acid and/or its salt are measured.

In the invention, the L value and the b value of the low-molecular-weight hyaluronic acid and/or its salt respectively refer to the L value and the b value of unpurified low-molecular-weight hyaluronic acid and/or its salt according to the invention obtained by a production method according to the invention described later. Specifically, the L value and the b value of the low-molecular-weight hyaluronic acid and/or its salt in the invention respectively refer to the L value and the b value of low-molecular-weight hyaluronic acid and/or its salt in a state in which the low-molecular-weight hyaluronic acid and/or its salt is not subjected to purification for decolorization. In the examples described later, the degree of coloration of the low-molecular-weight hyaluronic acid and/or its salt according to the invention refers to the L value and the b value of the low-molecular-weight hyaluronic acid and/or its salt in a state in which the low-molecular-weight hyaluronic acid and/or its salt is not subjected to purification other than washing using a medium in order to remove the acidic water-containing medium used.

The L value and the b value of the low-molecular-weight hyaluronic acid according to the invention may be measured using a color difference meter ("COLOR AND COLOR DIFFERENCE METER MODEL 1001 DP" manufactured by Nippon Denshoku Industries Co., Ltd.) in a state in which a 10-diameter lens is installed in the color difference meter and a glass cell is charged with 1 g or more of a measurement sample.

Since the low-molecular-weight hyaluronic acid and/or its salt according to the invention have an L value and a b value measured using the color difference meter of 90 or more and 5 or less, respectively, the low-molecular-weight hyaluronic acid and/or its salt can be used as a raw material for cosmetics, food, and medicine without requiring further purification.

The method of converting the low-molecular-weight hyaluronic acid according to the present invention to the low-molecular-weight hyaluronic acid salt and the method of converting the low-molecular-weight hyaluronic acid salt according to the present invention to the low-molecular-weight hyaluronic acid are not particularly limited. The low-molecular-weight hyaluronic acid and the low-molecular-weight hyaluronic acid salt may be converted using a known method.

As an example of the method of converting the low-molecular-weight hyaluronic acid according to the present invention to the low-molecular-weight hyaluronic acid salt, a method of treating the low-molecular-weight hyaluronic acid using an alkaline aqueous solution (e.g., aqueous solution of sodium hydroxide, potassium hydroxide, calcium hydroxide, magnesium hydroxide, ammonium hydroxide, or the like) can be given. As examples of the method of converting the low-molecular-weight hyaluronic acid salt according to the present invention to the low-molecular-weight hyaluronic acid, a method of treating the low-molecular-weight hyaluronic acid salt using an acidic aqueous solution (e.g., aqueous solution of hydrochloric acid, sulfuric acid, nitric acid, phosphoric acid, or the like) and a method using an acidic cation-exchange resin can be given.

When adding the low-molecular-weight hyaluronic acid and/or its salt according to the invention to cosmetics or food, the molecular weight of the low-molecular-weight hyaluronic acid and/or its salt is preferably 1,000,000 or less, more preferably 100,000 or less, still more preferably 20,000 or less, and most preferably 10,000 or less in order to achieve the objective property effects.

The method of measuring the molecular weight of the low-molecular-weight hyaluronic acid and/or its salt according to the invention is not particularly limited. For example, a method of calculating the limiting viscosity from the kinematic viscosity and converting the limiting viscosity into the molecular weight, a simple measuring method using liquid chromatography, and the like can be given.

In the invention, the molecular weight of the low-molecular-weight hyaluronic acid and/or its salt is measured using the method of calculating the limiting viscosity from the kinematic viscosity and converting the limiting viscosity into the molecular weight. In this method, the kinematic viscosity is measured using an Ubbelohde viscometer described later, the limiting viscosity is calculated from the kinematic viscosity, and the limiting viscosity is converted into the molecular weight.

The low-molecular-weight hyaluronic acid and/or its salt according to the invention preferably has a kinematic viscosity in a 1 mass % aqueous solution of 10 mm$^2$/s or less, more preferably 3 mm$^2$/s or less, and still more preferably 2 mm$^2$/s or less. If the low-molecular-weight hyaluronic acid and/or its salt according to the invention has a kinematic viscosity in a 1 mass % aqueous solution of more than 10 mm$^2$/s, preparation may become difficult due to too high a viscosity when adding the low-molecular-weight hyaluronic acid and/or its salt according to the invention in an amount exceeding a specific amount, or the viscosity of the resulting cosmetics or food may be affected, whereby the feel during use may deteriorate or the texture may be impaired.

1.3. Kinematic Viscosity Measuring Method

The method of measuring the kinematic viscosity used as the index when calculating the molecular weight of the low-molecular-weight hyaluronic acid and/or its salt according to the invention is described below.

The kinematic viscosity of the low-molecular-weight hyaluronic acid and/or its salt according to the invention may be measured using an Ubbelohde viscometer (manufactured by Sibata Scientific Technology Ltd.). In this case, an Ubbelohde viscometer is selected which has a coefficient so that the falling time is 200 to 1000 seconds. The kinematic viscosity is measured in a thermostat bath at 30° C. while maintaining a constant temperature.

The kinematic viscosity (mm$^2$/s) can be calculated from the product of the falling time (s) of the aqueous solution measured using the Ubbelohde viscometer and the coefficient of the Ubbelohde viscometer.

1.4. Calculation of Molecular Weight

In the invention, the molecular weight of the sample can be calculated from the limiting viscosity of the sample. In general, when calculating the limiting viscosity of the sample, a number of sample solutions are prepared, and the specific viscosity and the reduced viscosity are calculated from the falling time (s) of the sample solution and the falling time (s) of the solvent in the Ubbelohde viscometer according to the following expressions (1) and (2).

Specific viscosity=falling time (s) of sample solution/ falling time (s) of solvent−1 (1)

Reduced viscosity=specific viscosity/sample concentration (dried product) (g/100 mL) (2)

A calibration curve for each sample solution is created by plotting the reduced viscosity along the vertical axis and the sample concentration (dried product) along the horizontal axis, and the limiting viscosity of the sample is determined by extrapolating the sample concentration to zero. When the sample is hyaluronic acid and/or its salt, the molecular weight M of the sample can be calculated from the limiting viscosity of the sample according to the following expression (3).

Limiting viscosity (cm$^3$/g)=$k'M^{alpha}$ wherein k'=0.036, and alpha=0.78.

2. Method for Producing Low-Molecular-Weight Hyaluronic Acid and/or its Salt 2.1. Dispersion A method for producing low-molecular-weight hyaluronic acid and/or its salt according to the invention includes dispersing hyaluronic acid and/or its salt in an acidic water-containing medium. For example, the hyaluronic acid and/or its salt may be dispersed by adding powdered raw material hyaluronic acid and/or its salt to the acidic water-containing medium and stirring the mixture. The powdered hyaluronic acid and/or its salt is dispersed in the water-containing medium while being dissolved in the water-containing medium to only a small extent. Therefore, the powder precipitates when stirring is stopped.

A degree of reducing the molecular weight of the hyaluronic acid and/or its salt may be adjusted by adjusting the stirring speed and the stirring time. The period of time in which the hyaluronic acid and/or its salt is dispersed in the water-containing medium may be appropriately determined depending on the pH and the temperature of the water-containing medium.

Since the method for producing low-molecular-weight hyaluronic acid and/or its salt according to the invention includes dispersing the raw material hyaluronic acid and/or its salt in the water-containing medium, low-molecular-weight hyaluronic acid and/or its salt showing only a small degree of browning can be stably obtained. This makes purification for decolorization unnecessary, whereby a labor saving production process can be achieved.

In the method for producing low-molecular-weight hyaluronic acid and/or its salt according to the invention, the hyaluronic acid and/or its salt may be dispersed with heating. Specifically, the dispersion medium obtained by adding the powdered raw material hyaluronic acid and/or its salt to the acidic water-containing medium with stirring may be heated. Or, the acidic water-containing medium may be heated in advance, and the raw material hyaluronic acid and/or its salt may be added to the acidic water-containing medium while maintaining the temperature.

The heating temperature of the acidic water-containing medium is preferably 30 to 70° C. If the acidic water-containing medium is heated in this temperature range, the molecular weight of the hyaluronic acid and/or its salt can be stably reduced to a desired value by heating within one hour. The molecular weight of the raw material hyaluronic acid and/or its salt can also be reduced by dispersing the raw material hyaluronic acid and/or its salt at room temperature (less than 30° C.) without heating the acidic water-containing medium. In this case, a very long time may be required compared with the case of dispersing the raw material hyaluronic acid and/or its salt with heating. It is also possible to increase the heating temperature to more than 70° C. when dispersing the raw material hyaluronic acid and/or its salt. In this case, a reduction in molecular weight may progress to a large extent when the raw material hyaluronic acid and/or its salt is heated for a long period of time, whereby it may be difficult to stably adjust the molecular weight to a desired value.

2.2. Heating and Drying

The method for producing low-molecular-weight hyaluronic acid and/or its salt according to the invention may include heating and drying the residue obtained by removing the water-containing medium after dispersing the hyaluronic acid and/or its salt in the acidic water-containing medium.

For example, the residue obtained by removing the water-containing medium from the hyaluronic acid and/or its salt of which the molecular weight has been reduced by dispersion is heated and dried. The water-containing medium may be removed by a physical means such as filtration using a strainer or centrifugation, or by evaporation using a rotary evaporator, for example. It is preferable to remove the remaining water-containing medium and water from the residue using a heating cabinet, a hot blast dryer, or the like.

The heating and drying temperature and time are not particularly limited. The heating and drying temperature is preferably 60 to 95° C., more preferably 70 to 90° C., and still more preferably 70 to 80° C. If the heating and drying temperature is less than 60° C., the drying efficiency may decrease. If the heating and drying temperature exceeds 95° C., browning may occur. The heating and drying time is preferably 6 to 48 hours or more, and more preferably 12 to 36 hours. If the heating and drying time is less than 6 hours, the drying efficiency may decrease. If the heating and drying time exceeds 48 hours, browning may occur.

Since the molecular weight of the hyaluronic acid and/or its salt of which the molecular weight has been reduced by dispersion can be further reduced by heating and drying, the molecular weight reduction efficiency can be improved. A low-molecular-weight hyaluronic acid salt with a molecular weight of 100,000 and low-molecular-weight hyaluronic acid with a molecular weight of 20,000 or less can be easily obtained by heating and drying.

2.3. Water-Containing Medium

In the production method according to the invention, the term "water-containing medium" refers to a water-containing dispersion medium for hyaluronic acid and/or its salt. Hyaluronic acid and/or its salt preferably has a low solubility in the medium which may be used for the water-containing medium. The medium which may be used for the water-containing medium is not particularly limited. For example, a medium is preferred which is liquid, is soluble in water, and can be used in the production of cosmetics or food. Examples of the medium which may be used for the water-containing medium include alcohol media (e.g., methanol, ethanol, n-propanol, and 2-propanol), ketone media (e.g., acetone and methyl ethyl ketone), tetrahydrofuran, acetonitrile, and the like. These media may be used either individually or in combination of two or more. The medium is preferably at least one medium selected from ethanol, methanol, and acetone due to a low boiling point and low cost.

The water content of the water-containing medium is not particularly limited. If the water content is too high, hyaluronic acid and/or its salt cannot maintain a dispersion state and may be dissolved in the water-containing medium, whereby yield may decrease. Therefore, the content of water with respect to the total amount of the water-containing medium is preferably 40 vol % or less, and more preferably 30 vol % or less.

In the production method according to the invention, an acid or an acidic cation-exchange resin may be used to acidify the water-containing medium, for example.

The acid is not particularly limited. An acid is preferred which can be used in the production of cosmetics or food. Examples of the acid include inorganic acids such as hydrochloric acid, sulfuric acid, nitric acid, and phosphoric acid, and organic acids such as citric acid, ascorbic acid, acetic acid, and glacial acetic acid. The amount of acid to be added is not particularly limited. If the amount of acid is too small, a reduction in the molecular weight of hyaluronic acid and/or its salt may not sufficiently progress, whereby the production efficiency may decrease. If the amount of acid is too large, a reduction in the molecular weight of hyaluronic acid and/or its salt may be promoted, whereby it may be difficult to stably adjust the molecular weight to a desired value. For example, when using hydrochloric acid as the acid, the content of hydrochloric acid is preferably 0.2% or more and 4% or less. When using sulfuric acid as the acid, the content of sulfuric acid is preferably 0.1% or more and 3% or less.

The acidic cation-exchange resin is not particularly limited. Examples of the acidic cation-exchange resin include a strongly acidic cation-exchange resin (Diaion SK1B and Dowex 50W), a weakly acidic cation-exchange resin (Duolite C-464), and the like. Of these, the strongly acidic cation-exchange resin is preferred. For example, the molecular weight of the raw material hyaluronic acid and/or its salt can be reduced by securing the acidic cation-exchange resin in a container, placing the water-containing medium and the raw material hyaluronic acid and/or its salt in the container, dispersing the raw material hyaluronic acid and/or its salt, and causing the raw material hyaluronic acid and/or its salt to contact the acidic cation-exchange resin by stirring the dispersion medium. In this case, the acidic cation-exchange resin may be secured so that the acidic cation-exchange resin does not flow into the dispersion medium. The acidic cation-exchange resin and the resulting low-molecular-weight hyaluronic acid and/or its salt can be easily separated after the reaction by securing the acidic cation-exchange resin.

In the production method according to the invention, the pH of the water-containing medium is preferably 2 or less, and more preferably 1 or less. If the pH of the water-containing medium exceeds 2, it takes time to reduce the molecular weight of the raw material hyaluronic acid and/or its salt, whereby the efficiency decreases.

3. Cosmetics

The form of cosmetics including the low-molecular-weight hyaluronic acid and/or its salt according to the invention is not particularly limited. Examples of the form of the cosmetics include a skin cleansing preparation, toilet lotion, vanishing cream, cold cream, milky lotion, a pack, foundation, rouge, lipstick, nail cosmetics such as nail treatment, eye cosmetics such as mascara, shampoo, rinse, a hair treatment agent, shaving lotion, toothpaste, and the like.

4. Food Composition

The form of a food composition including the low-molecular-weight hyaluronic acid and/or its salt according to the invention is not particularly limited. Examples of the form of the food composition include general food such as staple food such as rice products and bread, dishes other than staple food such as retort (canned) food, frozen food, daily dishes, and dry food, seasoning such as mayonnaise, beverages, cake, dessert, and liquid, gelled, or soft-capsuled supplements, and general foods for specified health use for which use of health claims is allowed.

5. EXAMPLES

The invention is described below in more detail by way of examples, comparative examples, and experimental examples. Note that the invention is not limited to these examples. Measurement of kinematic viscosity, calculation of limiting viscosity, and measurement of the L value and the b value were conducted using the above-described methods.

5.1 Example 1

In this example, a sodium hyaluronate (hereinafter also called "HANa") fine powder extracted from a cockscomb and purified was provided as the raw material. The average molecular weight and the purity of the raw material HANa were respectively about 2,100,000 and 97%.

A tank (volume: 300 liters) equipped with a stirrer and a jacket was charged with 110 liters of 73% water-containing ethanol (acidic water-containing medium) containing 2% of hydrochloric acid. The water-containing ethanol was heated to 50° C. with stirring. Note that 73% water-containing ethanol contains 73% (W/W) of ethanol and 27% (W/W) of water, and 73% water-containing ethanol containing 2% of hydrochloric acid contains 2% (W/W) of hydrochloric acid and 98% (W/W) of 73% water-containing ethanol. After the temperature reached 50° C., 6 kg of the raw material HANa fine powder was added to the tank with stirring. The mixture was stirred so that the raw material HANa fine powder was dispersed while heating the mixture so that the temperature of the hydrochloric acid-and-water-containing ethanol was maintained at 50° C.

After 15 minutes of stirring, the mixture was allowed to stand. The supernatant hydrochloric acid-and-water-containing ethanol was then removed by decantation to obtain a precipitate. After the addition of 110 liters of 73% water-containing ethanol containing 2% of hydrochloric acid, which was heated to 50° C. in advance, to the resulting precipitate, the mixture was stirred for 15 minutes while heating the mixture at 50° C. This operation was carried out three times in total.

After the addition of 110 liters of 73% water-containing ethanol to the precipitate obtained after removing the hydrochloric acid-and-water-containing ethanol, the mixture was stirred for 15 minutes in order to remove the hydrochloric acid. This operation was repeated until the hydrochloric acid was completely removed.

The water-containing ethanol was then removed by decantation to obtain a residue. After further removing the water-containing ethanol by subjecting the residue to centrifugation, the solvent was removed at room temperature for six hours using a vacuum dryer.

5.5 kg (yield: about 92%) of low-molecular-weight hyaluronic acid was thus obtained as a fine white powder. The kinematic viscosity of a 1% aqueous solution of the resulting low-molecular-weight hyaluronic acid measured using an Ubbelohde viscometer was 2.6 mm$^2$/s. The molecular weight converted from the limiting viscosity was 35,000, the L value was 94.3, and the b value was 1.9.

5.2 Example 2

In this example, the HANa fine powder used in Example 1 was provided as the raw material.

A tank (volume: 300 liters) equipped with a stirrer and a jacket was charged with 110 liters of 80% water-containing acetone (acidic water-containing medium) containing 0.5% of sulfuric acid. The water-containing acetone was heated to 60° C. with stirring. Note that 80% water-containing acetone contains 80% (W/W) of acetone and 20% (W/W) of water, and 80% water-containing acetone containing 0.5% of sulfuric acid contains 0.5% (W/W) of sulfuric acid and 99.5% (W/W) of 80% water-containing acetone. After the temperature reached 60° C., 6 kg of the raw material HANa fine powder was added to the tank with stirring. The mixture was stirred so that the raw material HANa fine powder was dispersed while heating the mixture so that the temperature of the sulfuric acid-and-water-containing acetone was maintained at 60° C.

After 15 minutes of stirring, the mixture was allowed to stand. The supernatant sulfuric acid-and-water-containing acetone was then removed by decantation to obtain a precipitate. After the addition of 110 liters of 80% water-containing acetone containing 0.5% of sulfuric acid, which was heated to 60° C. in advance, to the resulting precipitate, the mixture was stirred for 15 minutes while heating the mixture at 60° C. This operation was carried out three times in total.

After the addition of 110 liters of 80% water-containing acetone to the precipitate obtained after removing the sulfuric acid-and-water-containing acetone, the mixture was stirred for 15 minutes in order to remove the sulfuric acid. This operation was repeated until the sulfuric acid was completely removed.

The water-containing acetone was then removed by decantation to obtain a residue. After further removing the water-containing acetone by subjecting the residue to centrifugation, the solvent was removed at room temperature for six hours using a vacuum dryer.

5.3 kg (yield: about 88%) of low-molecular-weight hyaluronic acid was thus obtained as a fine white powder. The kinematic viscosity of a 1% aqueous solution of the resulting low-molecular-weight hyaluronic acid measured using an Ubbelohde viscometer was 1.5 mm$^2$/s. The molecular weight converted from the limiting viscosity was 9,000, the L value was 94.0, and the b value was 2.9.

5.3 Example 3

The low-molecular-weight hyaluronic acid fine powder with a molecular weight of 26,000 obtained in Example 1 was heated and dried at 80° C. for 24 hours to obtain a fine white low-molecular-weight hyaluronic acid powder with a reduced molecular weight.

The kinematic viscosity of a 1% aqueous solution of the resulting low-molecular-weight hyaluronic acid measured using an Ubbelohde viscometer was 1.1 mm$^2$/s. The molecular weight converted from the limiting viscosity was 6,000, the L value was 93.9, and the b value was 3.2.

5.4 Example 4

In this example, a raw material hyaluronic acid (hereinafter also called "HA") fine powder was provided as the raw material which was extracted from a hyaluronic acid-containing fermented product obtained by culturing a hyaluronic acid-producing *Streptococcus* microorganism and then purified. The average molecular weight and the purity of the raw material HA were respectively about 1,600,000 and 97%.

A tank (volume: 300 liters) equipped with a stirrer was charged with 110 liters of 78% water-containing ethanol (acidic water-containing medium) containing 1% of hydrochloric acid. The water-containing ethanol was heated to 40° C. with stirring. Note that 78% water-containing ethanol contains 78% (W/W) of ethanol and 22% (W/W) of water, and 78% water-containing ethanol containing 1% of hydrochloric acid contains 1% (W/W) of hydrochloric acid and 99% (W/W) of 78% water-containing ethanol. After the temperature reached 40° C., 6 kg of the raw material HA fine powder was added to the tank with stirring. The mixture was stirred so that the raw material HA powder was dispersed while controlling the temperature so that the temperature of the hydrochloric acid-and-water-containing ethanol did not become less than 30° C.

After 15 minutes of stirring, the mixture was allowed to stand. The supernatant hydrochloric acid-and-water-containing ethanol was then removed by decantation to obtain a precipitate. After the addition of 110 liters of 78% water-containing ethanol containing 0.1% of hydrochloric acid, which was heated to 40° C. in advance, to the resulting precipitate, the mixture was stirred for 15 minutes while heating the mixture at 40° C. This operation was carried out twice in total.

After the addition of 110 liters of 78% water-containing ethanol to the precipitate obtained after removing the hydrochloric acid-and-water-containing ethanol, the mixture was stirred for 15 minutes in order to remove the hydrochloric acid. This operation was repeated until the hydrochloric acid was completely removed.

The water-containing ethanol was then removed by decantation to obtain a residue. After further removing the water-containing ethanol by subjecting the residue to centrifugation, the resulting product was dissolved in 100 liters of water in the tank to prepare an aqueous solution. The pH of the aqueous solution was adjusted to 6.5 by adding a 20% sodium hydroxide solution to the aqueous solution with stirring. The aqueous solution was then spray-dried using a spray dryer.

4.6 kg (yield: about 77%) of low-molecular-weight sodium hyaluronate was thus obtained as a fine white powder. The kinematic viscosity of a 1% aqueous solution of the resulting low-molecular-weight sodium hyaluronate measured using an Ubbelohde viscometer was 21 $mm^2/s$. The molecular weight converted from the limiting viscosity was 140,000, the L value was 95.0, and the b value was 1.8.

5.5 Example 5

The low-molecular-weight sodium hyaluronate fine powder with a molecular weight of 140,000 obtained in Example 4 was heated and dried at 80° C. for 24 hours to obtain a fine white low-molecular-weight sodium hyaluronate powder with a reduced molecular weight.

The kinematic viscosity of a 1% aqueous solution of the resulting low-molecular-weight sodium hyaluronate measured using an Ubbelohde viscometer was 8.7 $mm^2/s$. The molecular weight converted from the limiting viscosity was 41,000, the L value was 94.1, and the b value was 2.2.

5.6 Comparative Example 1

In this comparative example, a raw material was used which was prepared by immersing 200 kg of cockscombs in hot water at 80° C. for 20 minutes, finely grinding the cockscombs using a grinder, adding 500 liters of water to the resulting product, and forming a paste using a homogenizer.

A tank (volume: 1000 liters) equipped with a stirrer and a jacket was charged with the raw material. A 20% sodium hydroxide solution was added to the raw material so that the final sodium hydroxide concentration was 0.15 N. The solution was heated to 60° C. and maintained at 60° C. for two hours. The insoluble solid was removed from the solution by enzyme treatment and activated carbon treatment to obtain a filtrate. A cetylpyridinium chloride (CPC) solution was added to the filtrate so that a complex with hyaluronic acid was formed to obtain a precipitate.

After purifying the precipitate using ethanol, the solvent was removed at room temperature for six hours using a vacuum dryer.

2.0 kg (yield: about 1.0%) of low-molecular-weight sodium hyaluronate was thus obtained as a fine dark brown powder. The kinematic viscosity of a 1% aqueous solution of the resulting low-molecular-weight hyaluronic acid measured using an Ubbelohde viscometer was 21 $mm^2/s$. The molecular weight converted from the limiting viscosity was 140,000, the L value was 88.8, and the b value was 7.3.

5.7 Comparative Example 2

Low-molecular-weight sodium hyaluronate was obtained in the same manner as in Comparative Example 1 except for adjusting the final sodium hydroxide concentration to 0.1 N. The resulting low-molecular-weight sodium hyaluronate was dissolved in a 2% sodium chloride aqueous solution. After adjusting the pH of the hyaluronic acid-containing 2% sodium chloride aqueous solution to 2.5 by adding 4N hydrochloric acid, the mixture was heated at 95° C. for 120 minutes. After cooling the solution, ethanol was added to the solution to obtain a precipitate. After purifying the precipitate using ethanol, the solvent was removed at room temperature for six hours using a vacuum dryer.

0.9 kg (yield: about 0.5%) of low-molecular-weight hyaluronic acid was thus obtained as a fine dark brown powder. The kinematic viscosity of a 1% aqueous solution of the resulting low-molecular-weight hyaluronic acid measured using an Ubbelohde viscometer was 2.8 $mm^2/s$. The molecular weight converted from the limiting viscosity was 38,000, the L value was 87.2, and the b value was 5.6.

5.8 Comparative Example 3

1.0 kg (yield: about 0.5%) of low-molecular-weight hyaluronic acid was obtained as a fine dark brown powder in the same manner as in Comparative Example 2 except for changing the heating time under the alkaline conditions to 150 minutes. The kinematic viscosity of a 1% aqueous solution of the resulting low-molecular-weight hyaluronic acid measured using an Ubbelohde viscometer was 1.6 $mm^2/s$. The molecular weight converted from the limiting viscosity was 10,000, the L value was 87.0, and the b value was 6.5.

5.9 Experimental Example 1

As cosmetic formulation experimental examples, a whitening essence was prepared respectively containing the low-molecular-weight HA or HANa obtained in Examples 1 to 5 and Comparative Examples 1 to 3 according to the following formulation (internal volume: 50 mL/contained in a capped transparent glass bottle).

| <Formulation> | |
|---|---|
| Magnesium ascorbyl phosphate | 3.00% |
| Glycerol | 8.00% |
| 1,3-Butylene glycol | 2.00% |
| Hydrogenated lecithin | 0.05% |
| Low-molecular-weight hyaluronic acid (Na)[*1] | 0.50% |
| Hydroxyethylcellulose | 0.06% |
| PEG-50 hydrogenated castor oil | 0.50% |
| Sodium citrate | Proper quantity |
| Methylparaben | 0.21% |
| Phenoxyethanol | 0.08% |
| EDTA-4Na | 0.10% |

| <Formulation> | |
|---|---|
| Tocopherol | 0.05% |
| Water | Balance |

*¹Low-molecular-weight HA or HANa obtained in Examples 1 to 5 and Comparative Examples 1 to 3

In the experimental examples using the low-molecular-weight HA or HANa obtained in Examples 1 to 5, a transparent and colorless whitening essence exhibiting an excellent feel during use was obtained. In the experimental examples using the HA or HANa obtained in Comparative Examples 1 to 3, the resulting product was brown and was not suitable as a whitening essence.

5.10 Experimental Example 2

As cosmetic formulation Experimental examples, a milky lotion (emollient milk) was prepared respectively containing the low-molecular-weight HA or HANa obtained in Examples 1 to 5 and Comparative Examples 1 to 3 according to the following formulation (internal volume: 150 mL/contained in a capped transparent glass bottle).

| <Formulation> | |
|---|---|
| Stearic acid | 0.50% |
| Cetostearyl alcohol | 0.50% |
| Lanolin | 0.80% |
| Glycerol triisooctanoate | 4.00% |
| Olive oil | 4.00% |
| Low-molecular-weight hyaluronic acid (Na)*¹ | 1.00% |
| Polyoxyethylene (60) sorbitol tetraoleate | 0.50% |
| Polyoxyethylene (20) sorbitan monostearate | 1.00% |
| Glycerol monostearate | 0.50% |
| 1,3-Butylene glycol | 6.00% |
| Xanthan gum | 0.14% |
| Methylparaben | Proper quantity |
| Water | Balance |

*¹Low-molecular-weight HA or HANa obtained in Examples 1 to 5 and Comparative Examples 1 to 3

In the experimental examples using the low-molecular-weight HA or HANa obtained in Examples 1 to 5, a white milky lotion (emollient milk) exhibiting an excellent feel during use was obtained. In the experimental examples using the HA or HANa obtained in Comparative Examples 1 to 3, the resulting product was brown and was not suitable as a milky lotion.

5.11 Experimental Example 3

As food formulation experimental examples, a white peach jelly beverage contained in a spout pouch was prepared respectively containing the low-molecular-weight HA or HANa obtained in Examples 1 to 5 and Comparative Examples 1 to 3 according to the following formulation (internal volume: 150 g/contained in transparent spout pouch).

| <Formulation> | |
|---|---|
| Xanthan gum | 1.00% |
| Carrageenan | 0.50% |
| Low-molecular-weight hyaluronic acid (Na)*¹ | 0.20% |
| Dextrin alcohol | 3.00% |
| Sucralose | 0.02% |
| 4× concentrated white peach juice | 5.00% |
| Citric acid | 0.60% |

| <Formulation> | |
|---|---|
| Sodium citrate | 0.20% |
| L-Ascorbic acid | 0.10% |
| Peach essence | 0.20% |
| Water | Balance |

*¹Low-molecular-weight HA or HANa obtained in Examples 1 to 5 and Comparative Examples 1 to 3

In the experimental examples using the low-molecular-weight HA or HANa obtained in Examples 1 to 5, a white peach jelly beverage contained in a spout pouch exhibiting an excellent flavor and texture was obtained. In the experimental examples using the HA or HANa obtained in Comparative Examples 1 to 3, the resulting beverage was brown and was not suitable as a jelly beverage.

The invention claimed is:

1. A low-molecular-weight hyaluronic acid or its salt having a molecular weight of 6,000 to 100,000 daltons as measured by a limiting viscosity method, an L value indicating lightness of 90 or more, and a b value indicating hue of 5 or less,
the low-molecular-weight hyaluronic acid or its salt being obtained by a process comprising dispersing hyaluronic acid or its salt in an acidic water-containing medium having a pH of 2 or less, at a temperature of 30 to 70° C., wherein the water-containing medium contains at least one medium selected from the group consisting of ethanol, methanol, and acetone.

2. The low-molecular-weight hyaluronic acid or its salt according to claim 1, wherein the process further comprises removing the water-containing medium, and heating and drying a residue obtained after removing the water-containing medium.

3. The low-molecular-weight hyaluronic acid or its salt according to claim 1, wherein the molecular weight is in the range of 6,000 to 20,000 daltons as measured by a limiting viscosity method.

4. The low-molecular-weight hyaluronic acid or its salt according to claim 3, wherein the molecular weight is in the range of 6,000 to 10,000 daltons as measured by a limiting viscosity method.

5. The low molecular weight hyaluronic acid or its salt according to claim 1, wherein the molecular weight is in the range of 20,000 to 100,000 daltons as measured by a limiting viscosity method.

6. The low molecular weight hyaluronic acid or its salt according to claim 5, wherein the molecular weight is in the range of 20,000 to 41,000 daltons as measured by a limiting viscosity method.

7. The low molecular weight hyaluronic acid or its salt according to claim 6, wherein the molecular weight is in the range of 35,000 to 41,000 daltons as measured by a limiting viscosity method.

8. The low-molecular-weight hyaluronic acid or its salt according to claim 1, wherein the b value indicating hue is 4 or less.

9. The low-molecular-weight hyaluronic acid or its salt according to claim 8, wherein the b value indicating hue is 3.5 or less.

10. The low molecular weight hyaluronic acid or its salt according to claim 1, wherein a 1% aqueous solution of the low molecular-weight hyaluronic acid or its salt has a kinematic viscosity of 10 mm²/s or less.

11. The low-molecular-weight hyaluronic acid or its salt according to claim 6, wherein a 1 wt % aqueous solution of the low-molecular-weight hyaluronic acid or its salt has a kinematic viscosity of 3 mm$^2$/s or less.

12. The low-molecular-weight hyaluronic acid or its salt according to claim 11, wherein a 1 wt % aqueous solution of the low-molecular-weight hyaluronic acid or its salt has a kinematic viscosity of 2 mm$^2$/s or less.

13. A cosmetic comprising the low-molecular-weight hyaluronic acid or its salt according to claim 1.

14. A food composition comprising the low-molecular-weight hyaluronic acid or its salt according to claim 1.

15. A method for producing low-molecular-weight hyaluronic acid or its salt having a molecular weight of 6,000 to 100,000 daltons as measured by a limiting viscosity method, an L value indicating lightness of 90 or more, and a b value indicating hue of 5 or less, comprising dispersing hyaluronic acid or its salt in an acidic water-containing medium having a pH of 2 or less, at a temperature of 30 to 70° C., wherein the water-containing medium contains at least one medium selected from the group consisting of ethanol, methanol, and acetone.

16. The method for producing low-molecular-weight hyaluronic acid or its salt according to claim 15, further comprising removing the water-containing medium, and heating and drying a residue obtained after removing the water-containing medium.

17. The method for producing low-molecular-weight hyaluronic acid or its salt according to claim 15, wherein the content of water with respect to the total amount of the water-containing medium is 40 vol % or less.

\* \* \* \* \*